United States Patent [19]
Newman et al.

[11] Patent Number: 5,918,260
[45] Date of Patent: Jun. 29, 1999

[54] GAS SENSOR WITH MULTI-LEVEL SENSITIVITY CIRCUITRY

[75] Inventors: Robert L. Newman, Osceola; John S. Duesler, Wakarusa, both of Ind.

[73] Assignee: CTS Corporation, Elkhart, Ind.

[21] Appl. No.: 08/872,987

[22] Filed: Jun. 11, 1997

[51] Int. Cl.$^6$ .......................... G01N 25/36; G01N 27/04; G08B 17/10
[52] U.S. Cl. ...................... 73/31.05; 73/23.2; 73/335.02; 73/25.01; 422/96
[58] Field of Search ................................ 73/31.05, 23.31, 73/1 G, 23.28, 335.02, 23.21, 23.2, 25.01; 422/96, 95, 83

[56] References Cited

U.S. PATENT DOCUMENTS

| | | | |
|---|---|---|---|
| 3,886,786 | 6/1975 | Hoppesch et al. | 73/27 R |
| 4,237,721 | 12/1980 | Dolan | 73/23 |
| 4,258,002 | 3/1981 | Barr | 422/95 |
| 4,305,724 | 12/1981 | Micko | 23/232 E |
| 4,352,087 | 9/1982 | Wittmaier | 340/632 |
| 4,461,166 | 7/1984 | Gatten et al. | 73/27 R |
| 4,480,252 | 10/1984 | Buonavita | 340/632 |
| 4,533,520 | 8/1985 | Bossart et al. | 422/96 |
| 4,574,264 | 3/1986 | Takahashi et al. | 338/34 |
| 4,804,632 | 2/1989 | Schuck et al. | 436/143 |
| 4,818,977 | 4/1989 | Alexander | 340/633 |
| 4,829,810 | 5/1989 | Anderson et al. | 73/27 R |
| 4,847,783 | 7/1989 | Grace et al. | 364/497 |
| 4,854,155 | 8/1989 | Poli | 73/27 R |
| 4,938,928 | 7/1990 | Koda et al. | 422/96 |
| 5,055,269 | 10/1991 | Palumbo et al. | 422/96 |
| 5,057,436 | 10/1991 | Ball | 436/113 |
| 5,061,447 | 10/1991 | Ono | 422/96 |
| 5,087,574 | 2/1992 | Bell et al. | 436/120 |
| 5,225,786 | 7/1993 | Vaughn et al. | 324/706 |
| 5,297,419 | 3/1994 | Richardson | 73/25.03 |
| 5,363,091 | 11/1994 | Kotwicki et al. | 340/439 |
| 5,365,216 | 11/1994 | Kotwicki et al. | 340/439 |
| 5,379,630 | 1/1995 | Lacey | 73/25.03 |
| 5,517,182 | 5/1996 | Yasunaga | 340/634 |
| 5,526,280 | 6/1996 | Consadori et al. | 364/496 |
| 5,780,715 | 7/1998 | Imblum | 73/23.21 |

*Primary Examiner*—Hezron Williams
*Assistant Examiner*—J. David Wiggins
*Attorney, Agent, or Firm*—Michael W. Starkweather; Mark P. Bourgeois

[57] ABSTRACT

A combustible gas detector or sensors having a multi-level sensitivity circuitry. The gas detector has a bridge circuit for outputting voltages indicative of gas concentrations contacting the bridge circuit. There is a power supply node electrically coupled to one end of the bridge circuit. There is also a voltage control circuit, coupled between the bridge circuit and the power supply node, for controlling when at least a low and high input voltage level is supplied to the bridge circuit so that the bridge circuit has at least two levels of gas concentration discernability. The bridge circuit outputs distinguishable voltage levels for high gas concentrations in response to receiving the low voltage level. Additionally, the bridge circuit outputs distinguishable voltage levels for low gas concentrations in response to receiving the high voltage level.

11 Claims, 4 Drawing Sheets

GAS SENSOR WITH MULTI-LEVEL SENSITIVITY CIRCUITRY

CO-PENDING PATENT APPLICATIONS

This application is related to the following:

1) copending U.S. application Ser. No. 08/872,817, entitled, A GAS SENSOR WITH MULTIPLE EXPOSED ACTIVE ELEMENTS, attorney docket no. CTS-1508, filed Jun. 11, 1997,
2) copending U.S. application Ser. No. 08/873,219, entitled A GAS SENSOR WITH ORIENTATION INSENSITIVITY, attorney docket no. CTS-1509, filed Jun. 11, 1997, and
3) copending U.S. application Ser. No. 60/017,112, entitled, FUEL SYSTEM LOW CURRENT RHEOSTAT, attorney docket no. CTS-1491, filed May 9, 1996.

The aforementioned are assigned to the assignee named in the present application and are herein incorporated by reference in their entirety.

BACKGROUND OF THE INVENTION

1. Field of the Invention

This invention relates to the field of combustible gas detectors or sensors. Uniquely, the detector has multi-level sensitivity circuitry.

2. Description of the Related Art

Various devices are well known for combustible gas detectors used to detect the presence of combustible gases such as those found in car engines. Typical circuits are configured to include at least one sensing element that may be a wire having a catalytic coating. The sensing element was used as one of four legs of a wheatstone bridge circuit. The other three legs consisted of two resistors and a compensator element. The compensator element was identical to the sensing element except that it did not bear a catalytic coating.

A current or voltage was applied to the bridge circuit to heat the surface of the catalytic coating affixed to the sensing element. Since the resistance values of the other three legs of the bridge were known, the resistance in the sensing element could be determined as the current or voltage was passed through the bridge.

When the sensing element was exposed to a combustible gas, such as hydrocarbon, a reaction would occur, increasing the temperature of the sensing element. As the temperature of the sensing element increased, the resistance of the element increased. Accordingly, the current or voltage passing through the element decreased. By comparing the resistance level of the sensing element to the resistance level of the compensator element, the presence of a combustible gas could be detected. Since the amount of gas caused a nearly linear increase or decrease in the resistance of the sensing element, the quantity of the gas could be accurately determined by calibrating the change in resistance. This is the basic operating principle of a catalytic combustible gas sensor.

3. Related Art

Examples of patents related to the present invention are as follows, and each patent is herein incorporated by reference for the supporting teachings:

U.S. Pat. No. 5,526,280 is a method and system for gas detection.

U.S. Pat. No. 5,517,182 is a method for CO detection and its apparatus.

U.S. Pat. No. 5,379,630 is a thermal conductivity detector.

U.S. Pat. No. 5,365,216 is a catalyst monitoring using ego sensors.

U.S. Pat. No. 5,363,091 is a catalyst monitoring using ego sensors.

U.S. Pat. No. 5,297,419 is a linearizing gas analyzer.

U.S. Pat. No. 5,225,786 is a combustible gas sensor.

U.S. Pat. No. 5,087,574 is a fluid component detection method with feedback.

U.S. Pat. No. 5,057,436 is a method and apparatus for detecting toxic gases.

U.S. Pat. No. 5,055,269, is a temperature limited catalytic gas detector apparatus.

U.S. Pat. No. 4,938,928 is a gas sensor.

U.S. Pat. No. 4,847,783 is a gas sensing instrument.

U.S. Pat. No. 4,829,810 is a filament drive circuit.

U.S. Pat. No. 4,818,977, is a combustible gas detector having temperature stabilization capability.

U.S. Pat. No. 4,804,632 is a method for detecting combustible gases and device therefor.

U.S. Pat. No. 4,574,264 is a thin film oxygen sensor with microheater.

U.S. Pat. No. 4,533,520 is a circuit for constant temperature operation of a catalytic combustible gas detector.

The foregoing patents reflect the state of the art of which the applicant is aware and are tendered with the view toward discharging applicants' acknowledged duty of candor in disclosing information that may be pertinent in the examination of this application. It is respectfully stipulated, however, that none of these patents teach or render obvious, singly or when considered in combination, applicant's claimed invention.

4. Related Problem

Hydrocarbon sensors must measure gas concentrations in an exhaust stream environment that can range from a relatively low level to a very high level of gas concentrations, ie. 100 ppm to over 1000 ppm. The problem occurs when a designer must choose to build either a high or low level of gas concentration sensor. If a sensor is built to sense high concentrations, the resolution may typically be around 50 ppm, which is not very useful for sensing low concentrations of gas. If a low concentration sensor is built, the resolution may be as low as 1 ppm, but the sensor will saturate and not be able to sense high concentrations of gas. Therefore, a need exists for a sensor that can accommodate many different ranges of gas concentrations accurately.

This and other problems will be solved by the preferred embodiments of the invention. A review of the specification, drawings, and claims will more clearly teach a skilled artisan of other problems solved by the preferred embodiments.

SUMMARY OF THE INVENTION

It is a feature of the invention to provide a combustible gas detector or sensors having a multi-level sensitivity circuitry. The gas detector has a bridge circuit for outputting voltages indicative of gas concentrations contacting the bridge circuit. There is a power supply node electrically coupled to one end of the bridge circuit. There is also a voltage control circuit, coupled between the bridge circuit and the power supply node, for controlling when at least a low and high input voltage level is supplied to the bridge circuit so that the bridge circuit has at least two levels of gas concentration discernability.

Another feature of the invention is that the bridge circuit outputs distinguishable voltage levels for high gas concentrations in response to receiving the low voltage level. Additionally, the bridge circuit outputs distinguishable voltage levels for low gas concentrations in response to receiving the high voltage level.

Yet a further feature of the invention is that it includes a control circuit, coupled to the output of the bridge circuit, for controlling when the low and high input voltages are applied to the bridge circuit, and for calculating first and second final voltages indicative of the gas concentration detected when the low and high input voltage level was supplied to the bridge circuit.

A further feature of the invention is that it has a holding circuit, electrically coupled between the bridge circuit and the control circuit, for holding the first and second final voltage levels.

Still an additional feature of the invention is that it includes a first and second catalytic sensor element, located on the bridge circuit. Additionally, it includes a first and second reference sensor element, located on the bridge circuit and each respectively in series with the first and second catalytic sensor element. Wherein the first and second reference sensor elements are located to receive a same gas stream as the first and second catalytic sensor elements.

Additionally, it is a feature of the invention to have a base having one end for being heated during operation of the gas detector, the bridge circuit located on the one end thereof. Wherein during operation of the gas detector, a heated gas steam portion is created as the gas stream passes over the first and second catalyzed sensor element, the first and second catalyzed sensor element and the first and second sensor element are positioned on the base so that as the base rotates about the axis, the heated gas stream portion will not contact the first or second sensor element.

Moreover, a feature of the invention is that the base includes a catalyzed sensor section for mounting both the first and second catalyzed sensor elements on opposing sides thereof. Additionally, the base includes a sensor section for mounting both the first and second sensor elements on opposing sides thereof. Wherein the catalyzed sensor section and the sensor section has a void on at least two sides thereof.

The invention resides not in any one of these features per se, but rather in the particular combination of all of them herein disclosed and claimed. Those skilled in the art will appreciate that the conception, upon which this disclosure is based, may readily be used as a basis for the designing of other structures, methods and systems for carrying out the several purposes of the present invention. Further, the abstract is neither intended to define the invention of the application, which is measured by the claims, neither is it intended to be limiting as to the scope of the invention in any way.

Figure 1:
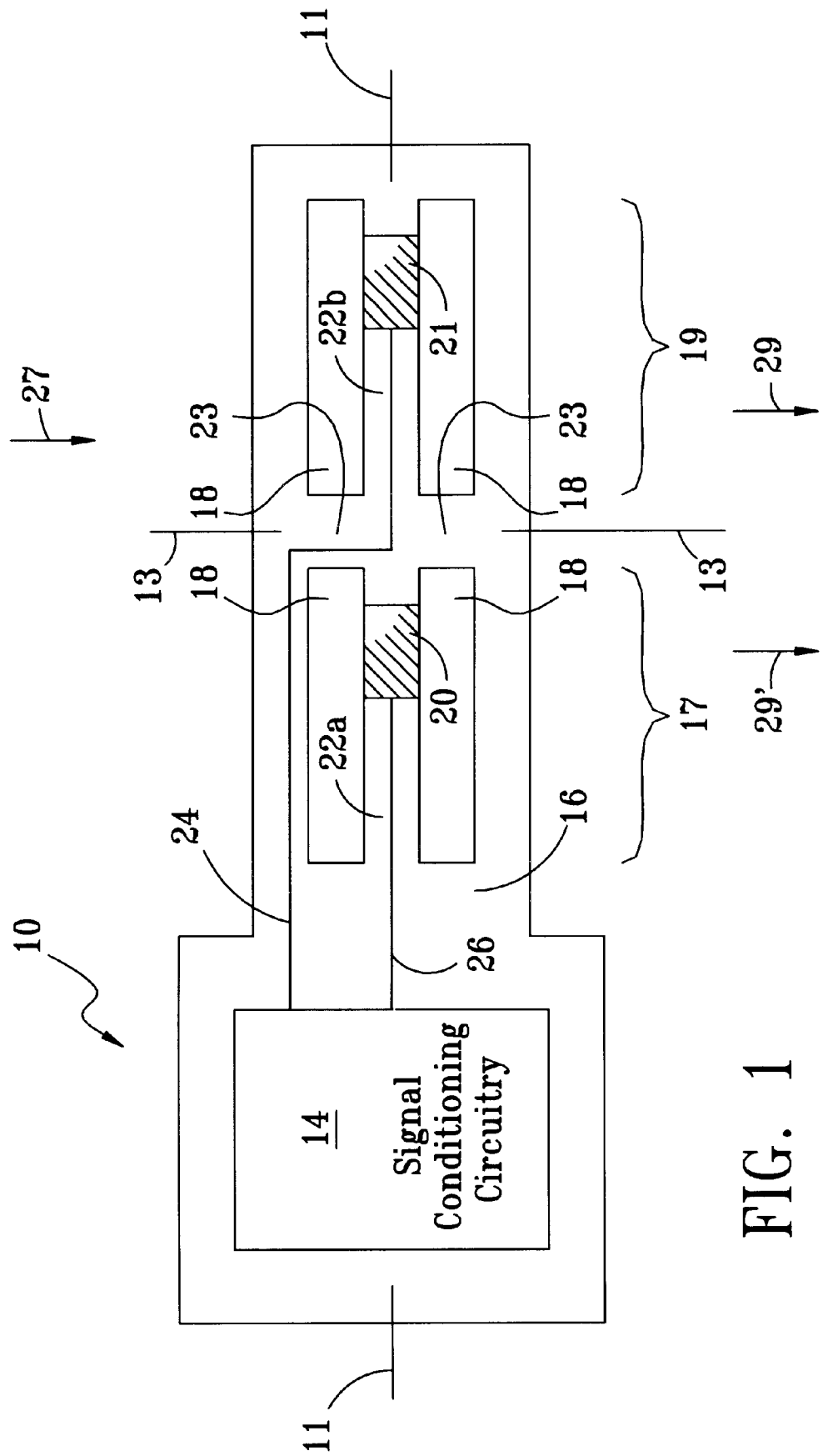
FIG. 1 is the preferred embodiment of the gas sensor circuitry design.

It is noted that the drawings of the invention are not to scale. The drawings are merely schematic representations, not intended to portray specific parameters of the invention. The drawings are intended to depict only typical embodiments of the invention, and therefore should not be considered as limiting the scope of the invention. In the drawings like numbering represents like elements between the drawings.

Detailed Description of the Preferred Embodiment

The present invention provides a gas sensor for determining gas concentrations in an air stream. Referring to FIG. 1, there is a preferred embodiment of the gas sensor 10. Specifically, the gas sensor 10 has a ceramic base 12, which has a longitudinal axis 11 oriented to be at an angle to the gas stream 27, illustrated as perpendicular. There is also a reference sensor element 20 on base 12, and a catalyzed sensor element 21 proximate the reference sensor element 20. As known in the art, the catalyzed sensor element 21 creates an exothermic reaction upon contacting the gas stream thereby forming a heated gas stream portion 29. The gas stream flowing past the reference sensor element 20 would not create a heated gas stream portion 29'. The base also has an extension portion 16, located between the signal conditioning circuitry 14 and the sensor regions 17, 19, for creating a distance between the circuitry 14 and the heated sensor regions 17, 19. Although extension portion 16 is illustrated as relatively short, in reality it could be relatively long to protect the circuitry 14 from the detrimental high temperatures associated with the operational temperature ranges of the sensor elements 20, 21. The sensor regions 17, 19 could be operating, for example, from 200 to 500 plus degrees Celsius for proper operation. However, the conditioning circuitry 14 would need to be operated around a maximum of 150 degrees Celsius for optimum signal processing. Thus, by regulating the length of extension section 16, it is possible to keep the signal conditioning circuitry 14 in a proper operational temperature range. An electrical connection 26 connects between reference sensor element 20 and circuitry 14, Similarly, an electrical connection 24 connects between catalyzed sensor element 21 and circuitry 14.

In the present embodiment, both sensor elements 20, 21 are located upon two separate bridge sections 22a, 22b. Additionally, these bridge sections are isolated from any heat sink effects from the base 12 by voids 18 located on at least either side of the bridges. In this arrangement, it is possible to have both sensor elements 20, 21 closer in temperature so that any change in electrical resistance would not be due to ambient gas stream heat. Thus, only exothermic heat from the catalytic reaction on the measuring sensor element will cause a notable difference between the two resistances of the two sensor elements. It is advantageous to have both sensor elements to be close in temperature to avoid having compensating circuitry and other means for adjusting for the temperature differences. With various designs of the bridges, voids, and sensor elements, it is possible to have temperature differences below 80 degrees Celsius and optimumly below 50 degrees Celsius when operating in 200 to 600 degrees Celsius or more. It is noted that the ideal situation would be to have no difference in temperature between the sensor elements except for the exothermic catalytic reaction effects.

Of particular note, horizontal axis 13 separates sensor regions 17 and 19. It is this separation that provides for the advantage of orientation insensitivity. Specifically, the sensor 10 may rotate about axis 11 and in no position will the heated gas stream portion 29 affect the reference non-catalyzed sensor 20. Of course, this situation only works if the gas stream is substantially perpendicular to the longitudinal axis 11. Also keep in mind that the gas stream most likely will already be heated but a skilled artisan will realize that the catalytic reaction with the gas will further heat the gas stream, thus creating the "extra" or catalyticly heated gas stream portion 29.

Figure 2:
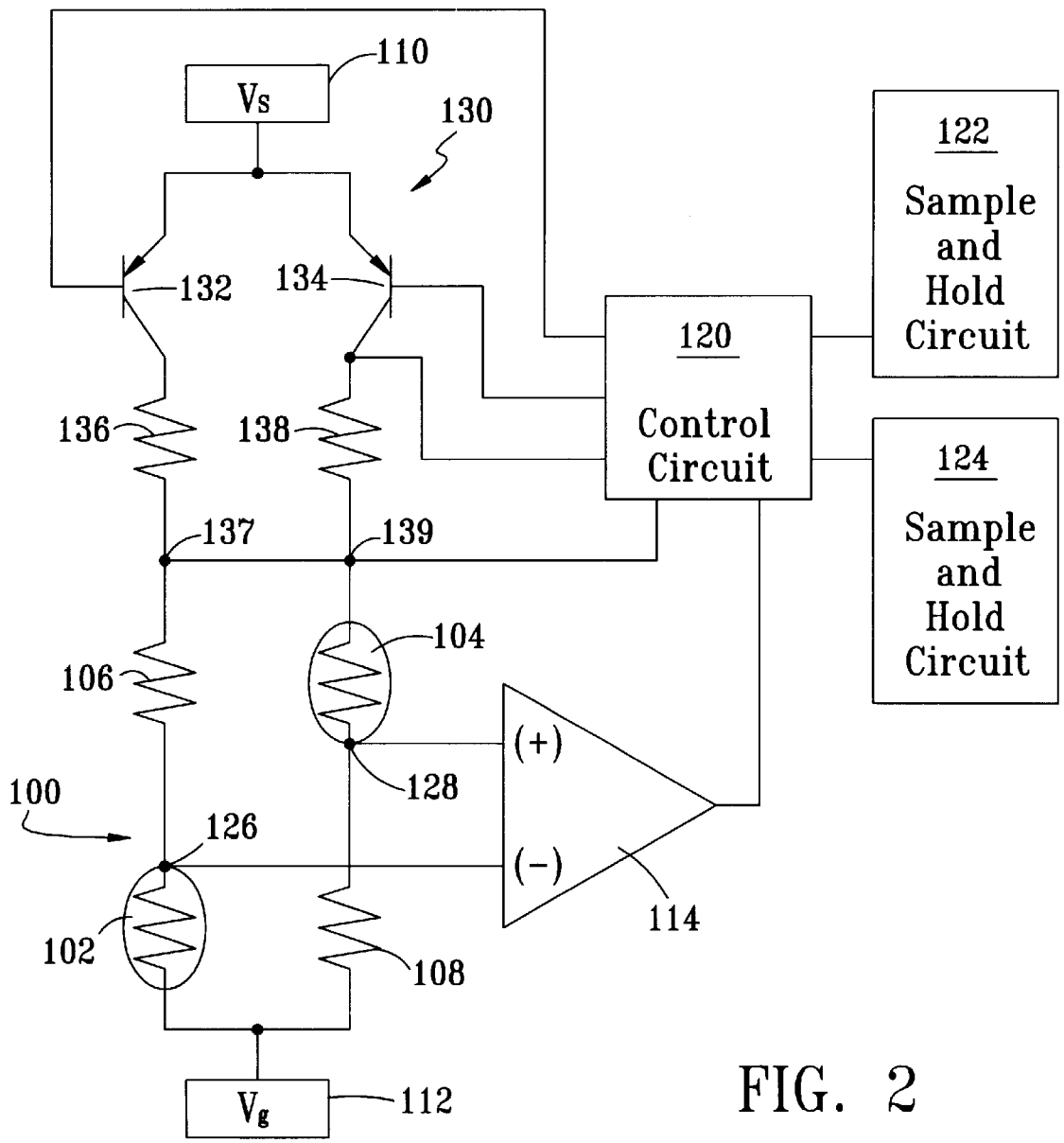
FIG. 2 is an electrical schematic of the preferred embodiment of the gas sensor circuitry.

Referring to FIG. 2, there is illustrated a preferred wheatstone bridge multi-level sensitivity circuit embodiment. Specifically, at the heart of the invention there is a wheatstone bridge circuit 100 having a first and second catalyzed sensor element 102, 104, a first and second non-catalyzed sensor element 106, 108, a voltage source Vs 110, and a ground Vg 112. Coupled to each bridge of the wheatstone circuit 100 is an amplifier 114 for amplifying the analog signal. Control circuit 120, has many functions, one is for first receiving the amplified signals and converting them to a digital signal to be held by a sample and hold circuit 122 or 124.

Another function of the control circuitry 120 is to control the voltage supply control circuitry 130, which is coupled to wheatstone bridge 100. The voltage supply control circuitry 130 includes at least two similar parallel bridges each including a transistor 132, 134, and a resistor 136, 138, which are coupled in series and between the supply node Vs 110 and the wheatstone bridge circuit 100.

One skilled in the art will realize the advantage of providing a multi-stage voltage supply control circuit 130. Specifically, by regulating the size of the devices, transistors and especially resistors, different amounts of voltage can be supplied to the sensing circuitry, which is the wheatstone bridge circuit 100, and thereby effect the output ranges of the general gas sensor circuitry. For example, the resistors are chosen so the applied bridge 100 voltage is a specific fraction of the voltage applied when the transistor is energized (eg. 1 volt compared to 10 volts). Since the amplifier 114 output is proportional to the bridge voltage, the output is reduced by a factor of ten when a transistor (132 or 134) is energized. This effectively makes the sensor able to measure gas concentrations of ten times larger without maximizing the amplifier output. The advantage is that a multiple range sensor can be designed by sequencing various bridge 100 voltages while using a low cost fixed gain amplifier 114 for the differential reading.

Figure 3:
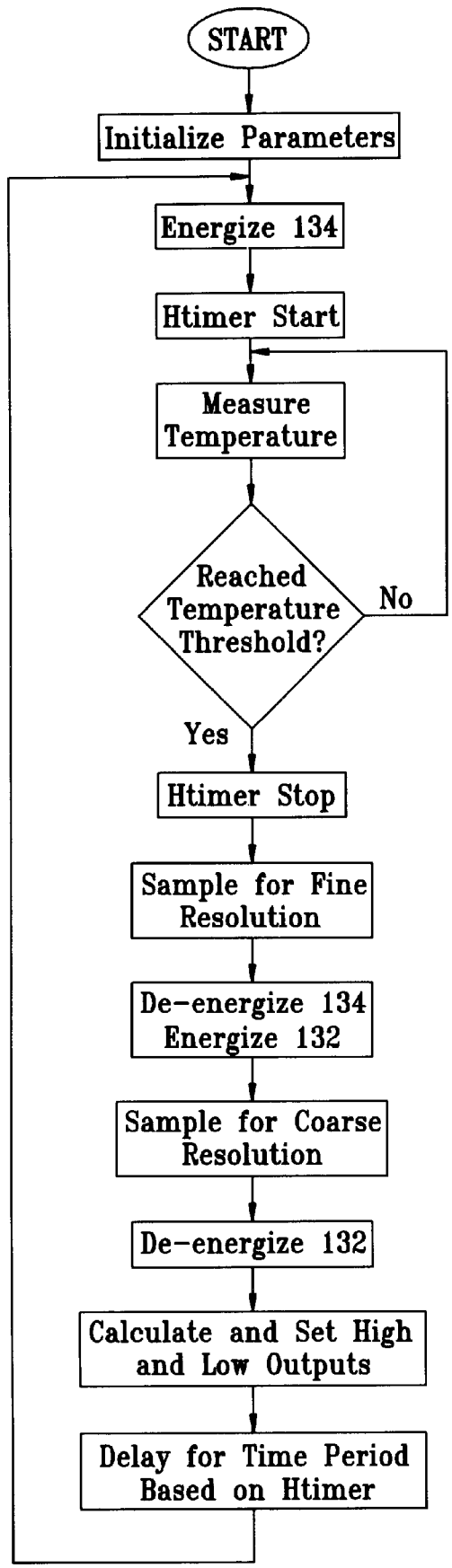
FIG. 3 is a flow chart of the operation of the circuitry of FIG. 2.

Referring to FIG. 3, there is a flowchart illustrating the method of dual range sensor control for the circuit in FIG. 2. Specifically, after the circuit is powered and initialization of parameters has finished, transistor 134 is energized to provide a relatively high voltage to bridge 100 through resistor 138. Simultaneously, controller 120 starts a heating timing sequence (Htimer Start) that both maintains a high voltage to bridge 100 for a fine resolution reading and heats the bridge 100 elements to allow the catalyst to reach a more reactive temperature. The controller 120 monitors the voltage at node 135 and across the bridge at nodes 137 and 139 to determine when the desired bridge temperature has been reached. Controller 120 monitors the time required to heat the bridge 100 and stops the heating timing sequence (Htimer Stop) at the appropriate time to start a cooling part of the sequence.

After heating of the bridge 100 is finished, a sample for fine and course resolution is taken. Next, sampling takes place for fine resolution, which best indicates low gas concentrations. During this sampling, transistor 134 remains activated, and the controller 120 stores both the amplified voltage from amplifier 114 and the voltage across the bridge at nodes 137 and 139 for later use.

The controller 120 then de-energizes transistor 134 and energizes transistor 132 to set up a lower voltage across bridge 100. Next, sampling takes place for low or course resolution, which best indicates high gas concentrations. Controller 120 stores the amplified voltage and the voltage across the bridge 100, then de-energizes transistor 132.

After controller 120 has collected the appropriate samples from the two voltage level inputs, two final voltage levels are calculated indicative of the gas concentration. Of course one of the final voltages will not be as discernable as the other because of the inherent resolution differences for different gas concentrations. These two final voltages are set on the high and low gas concentration output pins 122, and 124 respectively. The high and low outputs are calculated from the measurement of the amplifier output. The fine and coarse outputs are calibrated with an offset and gain value established during the manufacture of the device. Before calibration, the output of the amplifier may have arbitrary zero value and full scale value. Thereafter, the cycle begins again, after a delay based on the amount of time required for the heating and cooling sequence (Htimer or Heating Timer) is finished. For example, the following chart illustrates the amplifier output needed to get the desired output which indicates the gas concentration in parts per million (ppm): [note: Desired Output=(Amplifier Output+Offset)* Gain]

|  | Amplifier Output (v) | | Desired Output (v) | |
| --- | --- | --- | --- | --- |
| Gas Concentration (ppm) | Fine | Coarse | Fine | Coarse |
| 0 | 0.5 | 0.05 | 0 | 0 |
| 100 | 7 | 0.7 | 10(max) | 1 |
| 1000 | 10(max) | 6.55 | N/A | 10(max) |
|  | OFFSET | | GAIN | |
| FINE: | −0.5 | | 1.538 | |
| COARSE: | −0.05 | | 1.538 | |

Figure 4:
FIG. 4 is a graph illustrating potential gas concentration.

Referring to FIGS. 4–8, there is illustrated an example of the sensor 10 operation. In particular, it is illustrated that the fine resolution output range operates best from zero to 100 ppm (parts per million), and the coarse resolution output range operates best from 100 to 1000 ppm. FIG. 4 illustrates potential gas concentrations over 10 time periods.

Figure 5:
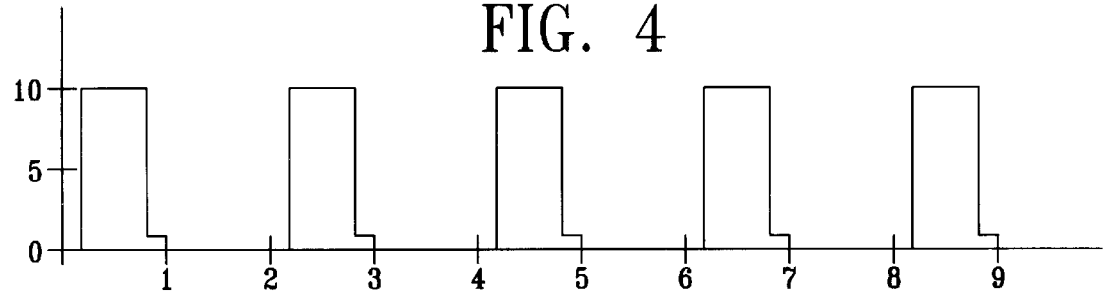
FIG. 5 is a graph illustrating voltages input to the preferred embodiment.

FIG. 5 illustrates two voltages, 1V and 10V, which are periodically and sequentially applied by the voltage control circuitry 130 to the bridge circuitry 100 to get a factor of 10 difference in the readings, ie. 100 and 1000 ppm maximum reading levels.

Figure 6:
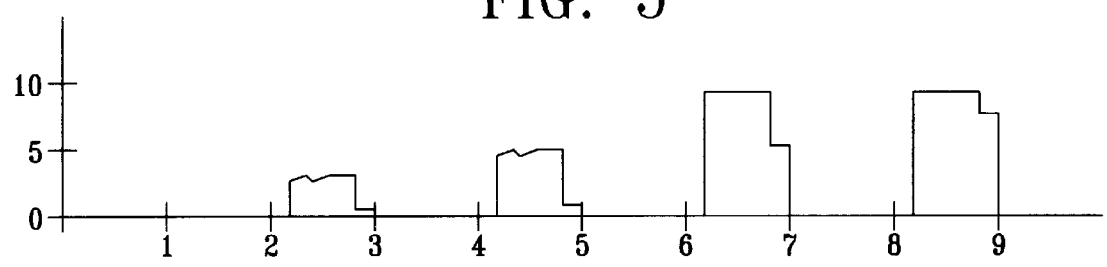
FIG. 6 is a graph illustrating the output voltages from the preferred embodiment.

FIG. 6 illustrates the output from amplifier 114, which reflects gas concentrations, resulting from the 1V and 10V inputs to bridge 100. Note, the fine resolution output, resulting from the 10 volt input, will rail at 10 volts when the gas concentration exceeds 100 ppm. However, the coarse resolution output, resulting from the 1 volt pulse input, will not rail until reaching to 1000 ppm in this example.

Figure 7:
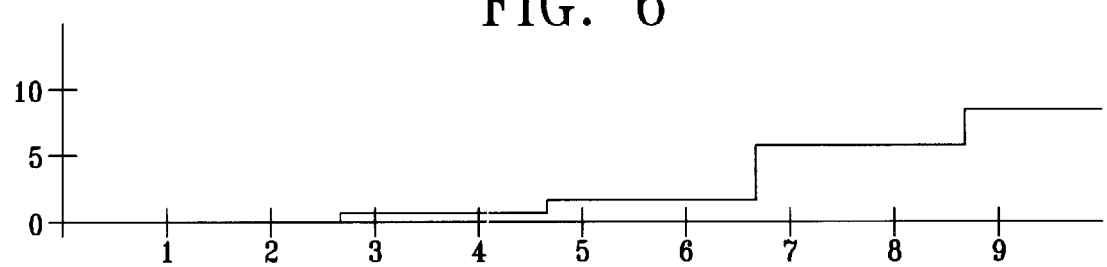
FIG. 7 is a graph illustrating output voltage from the preferred embodiment for high gas concentrations.

FIG. 7 illustrates the voltage in the high gas concentration coarse resolution sample and hold circuit 122. Note, the readings below 100 ppm are relatively indiscernible, but once they exceed 100 ppm the voltages are readable.

Figure 8:
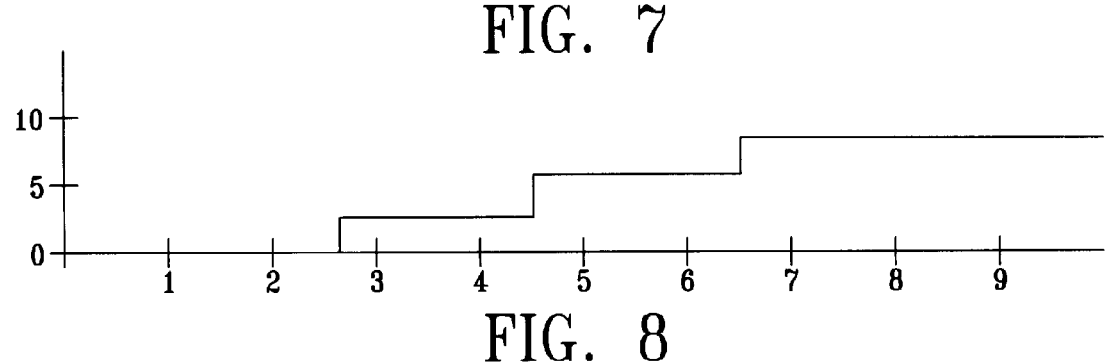
FIG. 8 is a graph illustrating output voltage from the preferred embodiment for low gas concentrations.

FIG. 8 illustrates the voltage in the low gas concentration fine resolution sample and hold circuit 124. Note, the readings below 100 ppm are readable, but the readings are indistinguishable and are railed for 100 ppm and higher gas concentrations.

Remarks about the Preferred Embodiment

The two catalyzed sensor elements 102, 104 are located on opposite sides of the base 12 but on the same bridge 22b, for example. The reference sensor elements 106, 108 are similarly arranged on opposite sides of the same bridge, for example bridge 22a. Thus, all four sensor elements will be located on the end of the sensor 10 that will receive direct impact from the gas stream 27. Of course, although the specification discusses the use of sensor elements, one skilled in the art realizes that each sensor 102, 104, 106, and 108, may be a resistor.

One skilled in the art of designing sensor circuitry will understand that the circuit 100 will create a doubling of the output to the amplifier 114. In operation, there are two basic conditions—inactive and active. When circuit 100 is inactive or in a starting condition, all four resistors are set to be equally charged to achieve a balanced grid. Thus, when current is applied to each side of the wheatstone bridge 100, the voltage at nodes 126 and 128 are equal.

When circuit 100 is active or when a gas stream is applied to circuit 100, there is an increase in the temperature on resistor 102 and 104, but no change to 106 and 108. As discussed previously, as the temperature increases, the resistance increases. Thus, the resistances on the catalyzed resistors are greater than resistances on non-catalyzed resistors. In an ideal setting, the resistance between the catalyzed resistors is equal, just as it should be for the non-catalyzed resistors. Because of the increased resistances, the voltage at node 128 is less than it was before the gas was applied. However, the voltage on node 126 is greater than it was before the gas was applied, because the resistance on resistor 102 is greater than resistor 106. In the ideal setting both nodes change the same amount but in opposite directions.

It is noted that in the prior art there is typically only one reference and one catalyzed sensor element and the other two resistors are fixed. It did not matter if the fixed resistors were in the bottom or the top or either side of the bridges, there would still be a shift in voltage, but it would only be one half the shift achieved by the preferred embodiment.

It is noted that the prior art has two of the wheatstone bridge resistors fixed. In other words, the fixed resistors are away from the gas and even in another chamber or on the circuit board, outside the heated environment. Thus, the prior art needs very precise temperature compensating circuitry to balance the bridges.

In the current preferred embodiment, no temperature compensating circuitry need be added to the sensor 10. By having all four resistors 102, 104, 106, and 108 in the heated gas stream, control of the temperature on all four resistors is achieved as a group. Temperature controlling circuitry is used, but the resistors on the wheatstone bridge circuit are used to create the heat by controlling the amount of current that flows therethrough. In the present design, the temperature of the sensor element doesn't have to be as accurately controlled as the prior art designs. The current invention does set a temperature, it is important to have elevated temperatures, but it is not needed to have the temperature exactly controlled, like 400 or 401 degrees Celsius. It is allowable to have, for example 400, 410 or 420 degrees Celsius and still have accurate readings, because all of the resistors are dimensionally and chemically equal. With the prior art, to have a balanced bridge, it is mandatory to accurately control the temperature of the two non-fixed resistors—the catalyzed and reference resistors. Thus, the prior art uses heaters in the designs.

The preferred embodiment will operate over a temperature range from as low as the light off temperature of the gas to be sensed to as high as whatever temperature that would breakdown the resistance of the resistors in the wheatstone bridge. The light off temperature is that temperature needed for a gas to interact with the catalyst to create an exothermic reaction.

In operation, the preferred embodiment does use a set temperature for the sensor to operate at high temperatures. In particular, it is best to operate at temperatures hotter than the ambient temperature. The hotter than ambient controlled temperature provides a stable output. One skilled in the art will realize that resistors have the resistance change linearly as a function of increasing temperature. However, for elevated temperatures, there is a little curve to the linear function. The difference in resistance that you get for a given temperature change, gets less and less as you increase hotter and hotter. Therefore, a fixed temperature is chosen higher than expected ambient because to follow a changing high ambient temperature would lead to a gradually decreased output signal as the temperature got hotter and hotter. Thus, a predictable output signal is achieved by setting the temperature of the sensor elements to a consistent output of volts per part per million.

To achieve the relatively fixed elevated temperature, the preferred embodiment has regulated current running through the bridge 100 to keep it at that selected temperature. Specifically, the resistors, which act as a heater when current goes through them, are turned on and off a proportional amount of time. A skilled artisan would know how to regulate the temperature by taking a voltage reading of nodes on either side of bridge 100 and setting the total resistance of bridge 100 by comparing it to the in series resistors 136 and 138.

One of the advantages of the preferred embodiment is that the selected temperature can be changed without changing any of the hardware, ie. resistors. Thus, by simply changing the timing programming of the heating current, most any temperature can be used for the same sensor and wheatstone bridge unlike the prior art that would require a changing of the physical resistors. A key to allowing this flexibility not previously found is that the present preferred embodiment uses the same material for each resistor, all resistors are heated the same way (in the heated gas stream 27), and trimmed to be dimensionally all the same.

Variations of the Preferred Embodiment

Although the illustrated embodiments discuss the arrangement of the sensor and signal conditioning circuitry 14 to be on a single base, one skilled in the art will realize that the preferred embodiment would work with most any arrangement. For example, the signal conditioning circuitry 14 could be on a separate base, where the sensor element containing base is, for example, solder connected to the signal conditioning circuit containing base. Additionally, the second base containing the conditioning circuitry could also be a printed circuit board and not ceramic material like the sensor element base.

Eventhough the disclosure discusses the sensing of hydrocarbon, one skilled in the art of gas sensors would understand that this invention is applicable to any gas that is needed to be detected. For example, if hydrogen were to be detected, the heating fixed target temperature for the sensor elements could be around 100 degrees Celsius. An application for a hydrogen sensor would be around a battery enclosure. A set of batteries on an electric car could use a sensor to monitor explosive fumes.

Although the preferred embodiment discusses the location of the catalyzed sensor element to be closest to the far end of the sensor, ie. sensor element 21, it is equally workable to have the catalyzed sensor to be located furthest away from the top of the sensor base, ie. sensor elements' 20 location. Thus, a reversal of the positions of the sensor elements is often needed dependent upon the orientation of the overall gas sensor in the gas stream. In these variations, it is still possible to have the heated gas stream portion 29 not contact the reference sensor elements 20 or 21 dependent upon the orientation design.

A further variation of the preferred embodiment is to have the longitudinal axis at most any angle to the gas stream that would allow rotation about the axis that would not have the catalyzed heated gas stream portion contact the reference sensor. However, the present invention works especially well if the whole sensor were inserted into the gas stream at a right angle. However, for example, the sensor housing could be at an acute angle oriented any way in the gas stream. If oriented toward the gas stream, of course the catalyzed sensor would be located below the non-catalyzed sensor (ie. further away from the one end of the base). In this arrangement, the sensor base 12 could be rotated about the longitudinal axis without having the heated gas stream portion 29 contacting the reference sensor elements. If the acutely angled sensor housing were facing downstream, however, the catalyzed sensor element would have to be the top most element with the reference sensor receiving the gas stream 27 first.

A skilled artisan will easily modify the disclosed voltage control circuity 130 to include any number of gas sensitivity stages. This is accomplished by providing several parallel circuits each with a separate control transistor in series with resistors of proportional or different resistances.

Although the preferred embodiment teaches that the bridge circuit 100 outputs discernable voltages in response to receiving high input voltages only when gas concentrations are low, it is within the realm of a skilled artisan to modify the circuitry to use low input voltages to get the same results. This variation holds equally true for accurately sensing high gas concentrations using high input voltages. The voltages selected is merely routine engineering.

While the invention has been taught with specific reference to these embodiments, someone skilled in the art will recognize that changes can be made in form and detail without departing from the spirit and the scope of the invention. The described embodiments are to be considered in all respects only as illustrative and not restrictive. The scope of the invention is, therefore, indicated by the appended claims rather than by the description. All changes that come within the meaning and range of equivalency of the claims are to be embraced within their scope.

We claim:

1. A gas detector having multiple gas detection levels, comprising:
    a) a bridge circuit for outputting voltages indicative of gas concentrations contacting the bridge circuit, having:
        a1) a first and second catalytic sensor element, located on the bridge circuit;
        a2) a first and second reference sensor element, located on the bridge circuit and each respectively in series with the first and second catalytic sensor element, the first and second reference sensor elements are located to receive a same gas stream as the first and second catalytic sensor elements;
    b) a power supply node electrically coupled to one end of the bridge circuit;
    c) a voltage control circuit, coupled between the bridge circuit and the power supply node, for controlling when at least a low and high input voltage level is supplied to the bridge circuit so that the bridge circuit has at least two levels of gas concentration discernability; and
    d) a base having one end for being heated during operation of the gas detector, the bridge circuit located on the one end thereof.

2. The gas detector of claim 1, wherein the bridge circuit outputing distinguishable voltage levels for high gas concentrations in response to receiving the low voltage level.

3. The gas detector of claim 2, wherein the bridge circuit outputing distinguishable voltage levels for low gas concentrations in response to receiving the high voltage level.

4. The gas detector of claim 1, further comprising:
    a control circuit, coupled to the output of the bridge circuit, for controlling when the low and high input voltages are applied to the bridge circuit, and for calculating first and second final voltages indicative of the gas concentration detected when the low and high input voltage level was supplied to the bridge circuit.

5. The gas detector of claim 4, further comprising:
    a sample and holding circuit, electrically coupled between the bridge circuit and the control circuit, for holding the first and second final voltage levels.

6. The gas detector of claim 5, wherein during operation of the gas detector, a heated gas stream portion is created as the gas stream passes over the first and second catalyzed sensor element, the first and second catalyzed sensor element and the first and second reference sensor element are positioned on the base so that as the base rotates about the axis, the heated gas stream portion will not contact the first or second reference sensor element.

7. The gas detector of claim 6, wherein the base includes a catalyzed sensor section for mounting both the first and second catalyzed sensor elements on opposing sides thereof.

8. The gas detector of claim 7, wherein the base includes a reference sensor section for mounting both the first and second reference sensor elements on opposing sides thereof.

9. The gas detector of claim 8, wherein the catalyzed sensor section and the reference sensor section has a void on at least two sides thereof.

10. A gas detector having multiple gas detection levels, comprising:
    a) a bridge circuit, located in a gas stream, for outputting voltages indicative of gas concentrations contacting the bridge circuit;
    b) a power supply node electrically coupled to one end of the bridge circuit;
    c) a voltage control circuit, coupled between the bridge circuit and the power supply node, for controlling when at least a low and high input voltage level is supplied to the bridge circuit so that the bridge circuit has at least two levels of gas concentration discernability;
    d) a first and second catalytic sensor element, located on the bridge circuit; and
    e) a first and second reference sensor element, located on the bridge circuit, each respectively in series with the first and second catalytic sensor element, during operation of the gas detector, a heated gas stream portion is created as the gas stream passes over the first and second catalyzed sensor element, the first and second catalyzed sensor element and the first and second reference sensor element are positioned on a base so that as the base rotates about an axis, the heated gas stream portion will not contact the first or second reference sensor element.

11. A gas detector having multiple gas detection levels, comprising:

a) a bridge circuit, mounted on a base and located in a gas stream, for outputting voltages indicative of gas concentrations contacting the bridge circuit;

b) a first and second catalytic sensor element, located on the bridge circuit;

c) a first and second reference sensor element, located on the bridge circuit and each respectively in series with the first and second catalytic sensor element, the first and second reference sensor elements are located to receive the same gas stream as the first and second catalytic sensor elements;

d) a power supply node electrically coupled to one end of the bridge circuit; and e) a voltage control circuit, coupled between the bridge circuit and the power supply node, for controlling when at least a low and high input voltage level is supplied to the bridge circuit so that the bridge circuit has at least two levels of gas concentration discernability.

* * * * *